United States Patent
Hall et al.

(10) Patent No.: US 7,986,822 B2
(45) Date of Patent: Jul. 26, 2011

(54) SYSTEM AND METHOD FOR X-RAY BASED ASSESSMENT OF ANEURYSM PULSATION

(75) Inventors: Andrew F Hall, St. Charles, MO (US); Ashraf Mohamed, Houston, TX (US); Teri Moore, Palo Alto, CA (US); Esther Rohm, Houston, TX (US); Frank Sauer, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1139 days.

(21) Appl. No.: 11/734,395

(22) Filed: Apr. 12, 2007

(65) Prior Publication Data

US 2009/0067568 A1    Mar. 12, 2009

Related U.S. Application Data (60) Provisional application No. 60/794,718, filed on Apr. 24, 2006.

(51) Int. Cl.
*G06K 9/00* (2006.01)
(52) U.S. Cl. ........................................ 382/128
(58) Field of Classification Search .......... 382/128–134; 128/920–925; 356/39–49; 600/407–414, 600/424–426; 345/581–618
See application file for complete search history.

(56) References Cited

U.S. PATENT DOCUMENTS

| | | | |
|---|---|---|---|
| 2003/0152519 A1* | 8/2003 | Koenig et al. | 424/9.41 |
| 2005/0251028 A1* | 11/2005 | Boese et al. | 600/425 |
| 2006/0100502 A1* | 5/2006 | Chen et al. | 600/419 |
| 2006/0210147 A1* | 9/2006 | Sakaguchi | 382/154 |
| 2007/0123771 A1* | 5/2007 | Redel et al. | 600/407 |
| 2008/0033302 A1* | 2/2008 | Grady et al. | 600/481 |

* cited by examiner

*Primary Examiner* — Samir A Ahmed
*Assistant Examiner* — Atiba O Fitzpatrick
(74) *Attorney, Agent, or Firm* — Donald B. Paschburg; F. Chau & Associates, LLC

(57) ABSTRACT

A method of assessing rupture risk of an aneurysm from time-resolved images includes injecting a contrast enhancing agent into a patient with an aneurysm, using an electrocardiogram (ECG) signal to trigger an image acquisition run, wherein a sequence of 2D X-ray fluoroscopic images is acquired along with a corresponding ECG signal value, rotating a C-arm attaching the X-ray fluoroscopic imaging apparatus during said image acquisition run, wherein the images in said X-ray fluoroscopic image sequence are acquired from a rotating viewpoint, sorting the images in said X-ray fluoroscopic image sequence into time windows of the cardiac cycle based on the ECG signal, and constructing one or more 3-dimensional (3D) angiography image volumes of said aneurysm from said 2D fluoroscopic image sequence.

20 Claims, 6 Drawing Sheets

SYSTEM AND METHOD FOR X-RAY BASED ASSESSMENT OF ANEURYSM PULSATION

CROSS REFERENCE TO RELATED UNITED STATES APPLICATIONS

This application claims priority from: "X-ray based assessment of aneurysm pulsation", U.S. Provisional Application No. 60/794,718 of Sauer, et al., filed Apr. 24, 2006, the contents of which are incorporated herein by reference.

TECHNICAL FIELD

This disclosure is directed to real-time X-ray fluoro imaging, in particular to time-resolved imaging of pulsating aneurysms.

DISCUSSION OF THE RELATED ART

An aneurysm (or aneurism) is localized, blood-filled dilation (bulge) of a blood vessel caused by disease or weakening of the vessel wall. Aneurysms can occur anywhere where there is a blood vessel, although they are most common in arteries. Aneurysms most commonly occur in arteries at the base of the brain, in the circle of Willis, and in the aorta, the main artery coming out of the heart. Rupture and blood clotting are the risks involved with aneurysms. This bulge in a blood vessel can burst and lead to death at any time, much like a bulge in an over-inflated innertube. Rupture leads to drop in blood pressure, rapid heart rate, and lightheadedness. The risk of death is high except for rupture in the extremities. The larger an aneurysm becomes, the more likely it is to burst. Aneurysms can be treated. Brain aneurysms are usually treated with stents, wire coils, or glue, with the intention to form a blood clot in the aneurysm that relieves the pressure against the aneurysm's wall.

The layer of the artery that is in direct contact with the flow of blood is the tunica intima, commonly referred to as the intima. This layer is made up of mainly endothelial cells. Adjacent to this layer is the tunica media, known as the media. This middle layer is made up of smooth muscle cells and elastic tissue. The outermost layer, that farthest from the flow of blood, is known as the tunica adventitia or the adventitia. This layer is composed of connective tissue.

Aneurysms can be broken down into two groups: true aneurysms and false aneurysms. A true aneurysm involves an outpouching of all three layers of the blood vessel: the intima, the media, and the adventitia. True aneurysms can be due to congenital malformations, infections, or hypertension. A false aneurysm, also known as a pseudoaneurysm, involves an outpouching of only the adventitia. Pseudoaneurysms can be due to trauma involving the intima of the blood vessel, and are a known complication of percutaneous arterial procedures. Aneurysms can also be described according to size: saccular or fusiform. A saccular aneurysm resembles a small sack, while a fusiform aneurysm is shaped like a spindle.

The most frequent site of aneurysm occurrence is in the anterior cerebral artery from the circle of Willis. The occurrence and expansion of an aneurysm in a given segment of the arterial tree involves local hemodynamic factors and factors intrinsic to the arterial segment itself. Aneurysm formation is probably the result of multiple factors affecting that arterial segment and its local environment.

The human aorta is a relatively low-resistance circuit for circulating blood. The lower extremities have higher arterial resistance, and the repeated trauma of a reflected arterial wave on the distal aorta may injure a weakened aortic wall and contribute to aneurysmal degeneration. Systemic hypertension compounds the injury, accelerates the expansion of known aneurysms, and may contribute to their formation.

Hemodynamically, the coupling of aneurysmal dilation and increased wall stress is approximated by the Laplace law, which states that the (arterial) wall tension is proportional to the pressure times the radius of the arterial conduit: $T=P \times R$. As diameter increases, wall tension increases, which contributes to increasing diameter. As tension increases, risk of rupture increases. Increased pressure, such as that due to systemic hypertension, and increased aneurysm size aggravate wall tension and therefore increase the risk of rupture.

Historically, the treatment of arterial aneurysms has been surgical-intervention, or watchful waiting in combination with control of blood pressure. Recently, endovascular or minimally invasive techniques have been developed for many types of aneurysms.

X-ray C-arms are routinely used in medicine to acquire images for diagnostic assessment of a patient's vascular structures, and for guidance of interventional therapeutic procedures such as stent placement or coiling of aneurysms.

Diagnostic applications include the acquisition of angiograms, 2D X-ray projection images of vascular structures filled with a contrast agent injected through a catheter. 3D angiograms can be obtained by rotating the X-ray C-arm, acquiring a set of angiograms as 2D projection images during the rotational run, and then reconstructing a 3D volume image from these set of projections. Digital subtraction angiography subtracts two X-ray images, one with and one without the contrast agent. The background anatomy cancels out, and the contrasted vessel is highlighted.

Interventional applications include the acquisition of fluoro images, which are low dose X-ray projection images, acquired to monitor the progress of a therapeutic procedure, e.g. to observe the progress of a guidewire or catheter insertion.

Risk assessment of aneurysms is an important topic. For example, how likely is an aneurysm to rupture? How urgent is the need for treatment? Recently, methods from computational flow dynamics have been suggested to study the flow inside the vascular structure and the aneurysm, in particular assess the stress on the vessel walls. In combination with bio-mechanical models of the vessel walls, the modeling can try to predict the risk of aneurysm rupture.

A patient specific vessel geometry can be derived from a 3D angiography image, alternately also from a 3D computed tomography angiography (CTA) image, computed with an injected contrast. The process is known as segmentation. Segmentation methods that extract the surface of inner vessel walls can, e.g., be based on region growing and other standard methods.

However, the correct modeling of the flow inside a vessel is impossible to validate in-vivo. In addition, patient-specific modeling of the mechanical properties of the vessel walls cannot be done at all based on the 3D Angiography or CTA images. Hence, improved in-vivo measurements of aneurysms would be useful.

SUMMARY OF THE INVENTION

Exemplary embodiments of the invention as described herein generally include methods and systems for the use of dynamic or time-resolved imaging of aneurysms that pulsate with the heartbeat as a means to derive important diagnostic information. Strong pulsation of aneurysms has been suggested to be an indication of vulnerability. According to embodiments of the invention, the dynamic information is used in different ways to make an assessment of aneurysm rupture risk.

According to an aspect of the invention, there is provided a method of assessing rupture risk of an aneurysm from time-resolved images including injecting a contrast enhancing agent into a patient with an aneurysm, acquiring a sequence of 2D X-ray images of said aneurysm over a cardiac cycle, extracting linear or area measurements of said aneurysm from said sequence of images, and correlating the extracted aneurysm measurement values to clinically known values to assess a rupture risk of said aneurysm.

According to a further aspect of the invention, the method comprises using an electrocardiogram (ECG) signal to trigger said acquisition of said image sequence.

According to a further aspect of the invention, the method comprises acquiring a plurality of image sequences from multiple viewpoints using the ECG trigger to establish correspondences between images from different sequences of said plurality of sequences in relation to a cardiac phase.

According to a further aspect of the invention, the method comprises using a sequence of corresponding image tuples from said different sequences to extract volume measurements of said aneurysm, and correlating these values to clinically known values to assess a rupture risk of said aneurysm.

According to a further aspect of the invention, the method comprises acquiring a sequence of background 2D X-ray images acquired without using said injected contrast enhancing agent, and subtracting said background images from said contrast enhanced images that correspond in relation to the cardiac phase.

According to a further aspect of the invention, the method comprises shifting a trigger point in the cardiac cycle for starting said image acquisition by a time shorter than an exposure time for a 2D X-ray image, and acquiring another sequence of images using said shifted trigger point.

According to a further aspect of the invention, the method comprises segmenting said aneurysm in each image of each of said image sequences and interpolating 2D segmented outlines into a 3D shape of said aneurysm.

According to a further aspect of the invention, the method comprises providing a bi-plane C-arm attaching X-ray imaging apparatus, adjusting a viewing direction of said C-arm for image acquisition, and acquiring pairs of images from different viewing directions and displaying said pair of images on different display monitors.

According to a further aspect of the invention, the method comprises adjusting a C-arm orientation after acquiring a sequence of images, wherein said C-arm attaches the X-ray imaging apparatus, and performing another sequence of image acquisitions.

According to a further aspect of the invention, the method comprises determining a variation over time of said linear or area measurements of said aneurysm by calculating a maximal relative change of each linear or area measurement.

According to a further aspect of the invention, the method comprises determining a variation over time of said volume measurements of said aneurysm by calculating a maximal relative change of said volume measurement.

According to a further aspect of the invention, the method comprises determining a degree of non-linear motion of said aneurysm as its linear or area measurements vary over time using said ECG signal to time resolve said acquired images.

According to another aspect of the invention, there is provided a method of assessing rupture risk of an aneurysm from time-resolved images including injecting a contrast enhancing agent into a patient with an aneurysm, using an electrocardiogram (ECG) signal to trigger an image acquisition run, wherein a sequence of 2D X-ray fluoroscopic images is acquired, along with a corresponding ECG signal value, rotating a C-arm attaching the X-ray fluoroscopic imaging apparatus during said image acquisition run, wherein the images in said X-ray fluoroscopic image sequence are acquired from a rotating viewpoint, sorting the images in said X-ray fluoroscopic image sequence into time windows of the cardiac cycle based on the ECG signal, and constructing one or more 3-dimensional (3D) angiography image volumes of said aneurysm from said 2D fluoroscopic image sequence.

According to a further aspect of the invention, the method comprises segmenting said aneurysm in said constructed 3D image, extracting linear, area, or volume measurements of said aneurysm from said segmented aneurysm, and correlating the extracted aneurysm measurement values to clinically known values to assess a rupture risk of said aneurysm.

According to a further aspect of the invention, the method comprises creating a mathematical model of the walls of the aneurysm, and of blood flow through said aneurysm, running said mathematical model wherein changes in the aneurysm model due to blood pressure changes are observed, comparing the modeled behavior of said aneurysm with corresponding measured behavior of an aneurysm, and refining parameters characterizing said aneurysm wall model and blood flow model, wherein rupture risk is assessed in terms of a stress and strain on a wall of said aneurysm.

According to another aspect of the invention, there is provided a program storage device readable by a computer, tangibly embodying a program of instructions executable by the computer to perform the method steps for assessing rupture risk of an aneurysm from time-resolved images.

DETAILED DESCRIPTION OF THE EXEMPLARY EMBODIMENTS

Exemplary embodiments of the invention as described herein generally include systems and methods for time-resolved imaging of pulsating aneurysms. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g. a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Fluoroscopy is a technique that provides moving projection radiographs of somewhat low quality. Fluoroscopy is mainly performed to view movement of tissue or a contrast agent, or to guide a medical intervention, such as angioplasty, pacemaker insertion, or joint repair/replacement. The latter are often carried out in an operating room, using a portable fluoroscopy machine called a C-arm. It can move around the surgery table and provide digital images for the surgeon.

Angiography is the use of fluoroscopy to view the cardiovascular system. An iodine-based contrast is injected into the bloodstream and observed as it travels around. Since liquid blood and the vessels are not very dense, a contrast with high density, such as iodine, is used to view the vessels using X-rays. Angiography can be used to find aneurysms, leaks, blockages, new vessel growth, and placement of catheters and stents.

Computed tomography (CT) scanning uses a large amount of ionizing radiation in the form of X-rays in conjunction with a computer to create images of both soft and hard tissues. These images look as though the patient was sliced like bread. Contrast agents are often used, depending on the tissues that need to be seen. Radiographers perform these examinations, sometimes in conjunction with a radiologist, for example, when a radiologist performs a CT-guided biopsy.

Digital Subtraction Angiography (DSA) is a procedure to visualize blood vessels with contrast medium in a bony environment by subtracting the pre-contrast image from the image with contrast medium. It is useful in diagnosing arterial occlusion, including carotid artery stenosis and pulmonary artery thrombosis, and in detecting renal vascular disease. After the contrast material is injected into an artery or vein, a physician produces fluoroscopic images.

In traditional angiography, images of blood vessels on films are acquired by exposing the area of interest with time-controlled X-ray energy while injecting contrast medium into the blood vessels. The images thus obtained would also record other structure besides blood vessels as the X-ray beam passes through the body. In order to remove these distracting structures to see the vessels better, one needs to acquire a mask images for subtraction. The mask image is simply an image of the same area without contrast administration. So, clear pictures of blood vessels are obtained by taking away the overlying background.

In DSA, the images are acquired in digital format through the computer. With the help of the computer, all images would be recorded into the computer and subtracted automatically. As a result, one can obtain a near-instantaneous film show of the blood vessels alone after X-ray.

Figure 1:
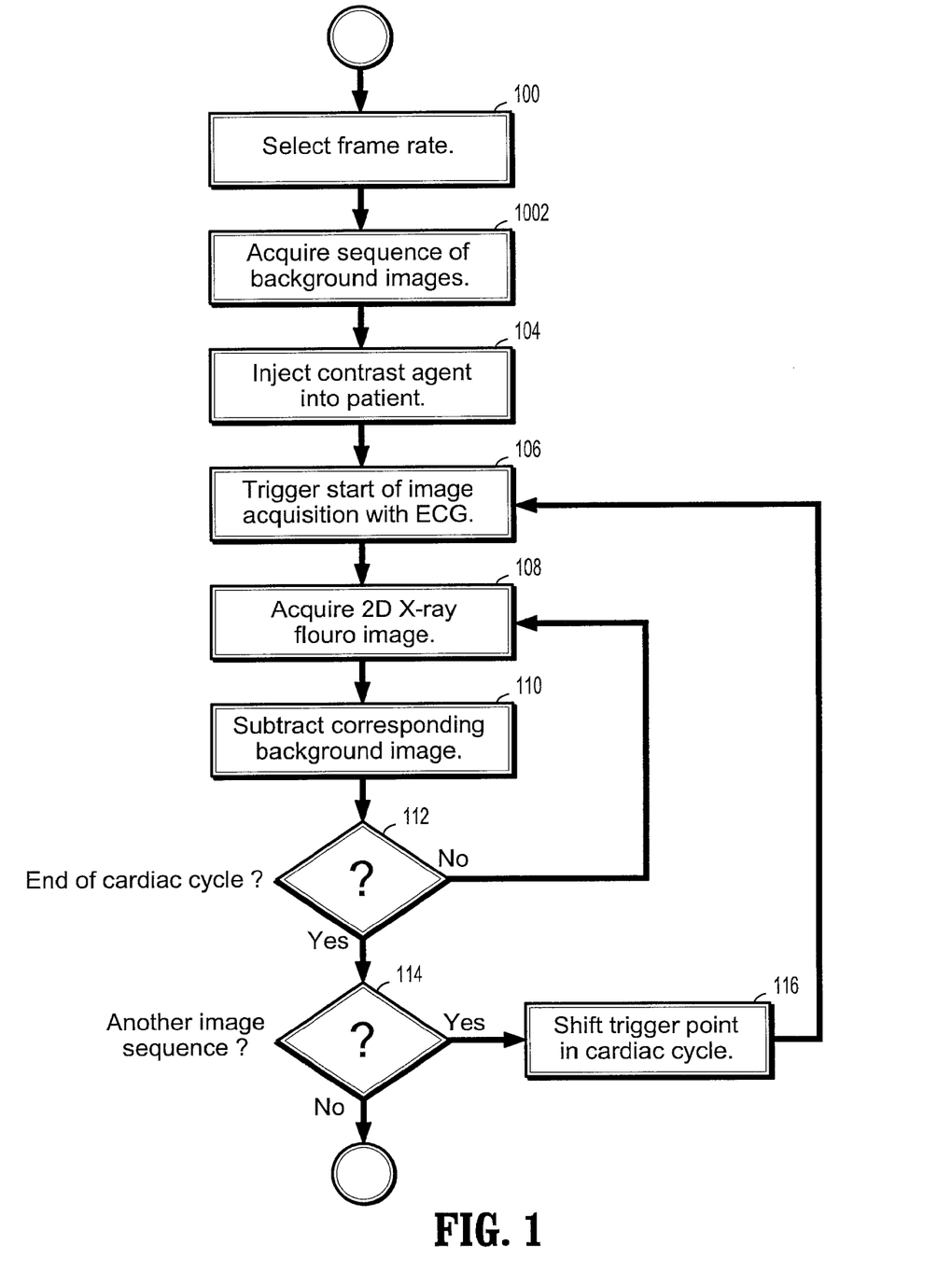
FIG. 1 is a flowchart of a method for acquiring a fluoro sequence in real-time over at least one cardiac cycle according to an embodiment of the invention.

According to an embodiment of the invention, FIG. 1 is a flowchart of a method for acquiring a fluoro sequence in real-time over at least one cardiac cycle to obtain a time resolved 2D image sequence of the aneurysm pulsation. Referring to the figure, a high speed frame rate of 15 frames per second or higher is selected at step 100 to time-resolve the aneurysm's motion. A sequence of background images is acquired at step 102. At step 104, a contrast agent is injected to make the aneurysm and the connected vascular structure visible in the X-ray images. This injection is maintained during the course of image acquisition. The start of the acquisition can be triggered at step 106 with a signal derived from the patient's electrocardiogram (ECG). During each frame, an image is acquired at step 108, and is displayed at step 110 on a display monitor. The ECG signal is also acquired and saved for subsequent analysis of the images. For better visibility of the aneurysm, the background image is subtracted from the displayed image. The background image would be acquired without the use of a contrast injection, as in the case of DSA. At step 112, the ECG is checked to see if the end of the cardiac cycle has been reached. If not, the image acquisition system loops back to repeat steps 108 to 112. At step 114, to catch the short moment of maximum extension of the aneurysm, another imaging run can be performed to acquire a fluoro sequence that covers another cardiac cycle. In this case, at step 116, the trigger point is shifted in time from cycle to cycle, by a time that is shorter than the exposure time of a single fluoro image. By repeating these steps, an imaging run over several cardiac cycles can be acquired.

Figure 2:
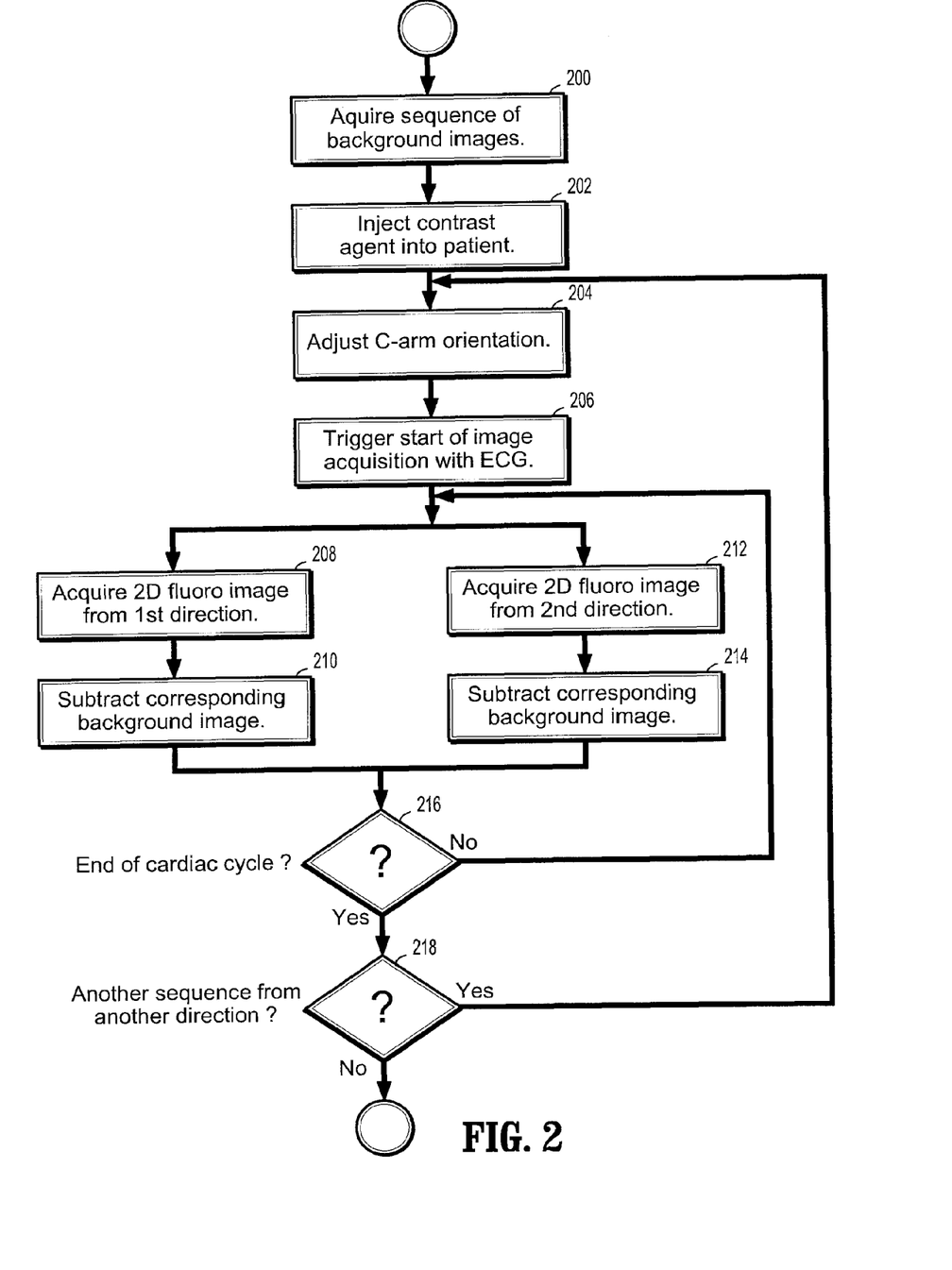
FIG. 2 is a flowchart of a method for acquiring a several fluoro sequences in real-time from different directions according to an embodiment of the invention.

According to another embodiment of the invention, FIG. 2 is a flowchart of a method for acquiring a several fluoro sequences in real-time from different directions. Once again, a sequence of background images is acquired at step 200 and at step 202, a contrast agent is injected so that the vessels of interest are visible during image acquisition. Two fluoro sequences can be acquired concurrently with a bi-plane C-arm system holding the flouro imaging apparatus, but also sequentially with a mono-plane C-arm system. For more than two different viewing directions, corresponding fluoro sequences can be acquired sequentially as standard C-arm systems do not have more than two source-detector pairs. At step 204, the user experimentally adjusts an orientation of the C-arm. It is desired to find a viewing direction that can show particularly large pulsations of the aneurysm. In an exemplary C-arm configuration, the aneurysm is imaged from the side so that aneurysm neck and connection to the vascular structure are quite visible, and from the top, with the vessel underneath and covered by the aneurysm. The start of the acquisition is triggered at step 206 with a signal derived from the patient's electrocardiogram (ECG). During each frame, the ECG signal is saved, an image is acquired from a first direction at step 208 and is displayed at step 210, and an image is acquired from a second direction at step 212 and is displayed at step 214. As before, the background image is subtracted from the images to be displayed. At step 216, the ECG is checked to see if the end of the cardiac cycle has been reached, after which, at step 218, if an image from another viewing direction is desired, the system returns to step 204 where the user re-adjusts the C-arm position. Another acquisition run is triggered at step 206, and the images are acquired and displayed, this time from only one direction, at steps 208, and 210, respectively, until the end of the cycle at step 216.

Note that, for a mono-plane C-arm system, the image acquisition system would skip steps 212 and 214, and images from the second C-arm orientation would be acquired and displayed in the second sequential cycle.

Figure 3:
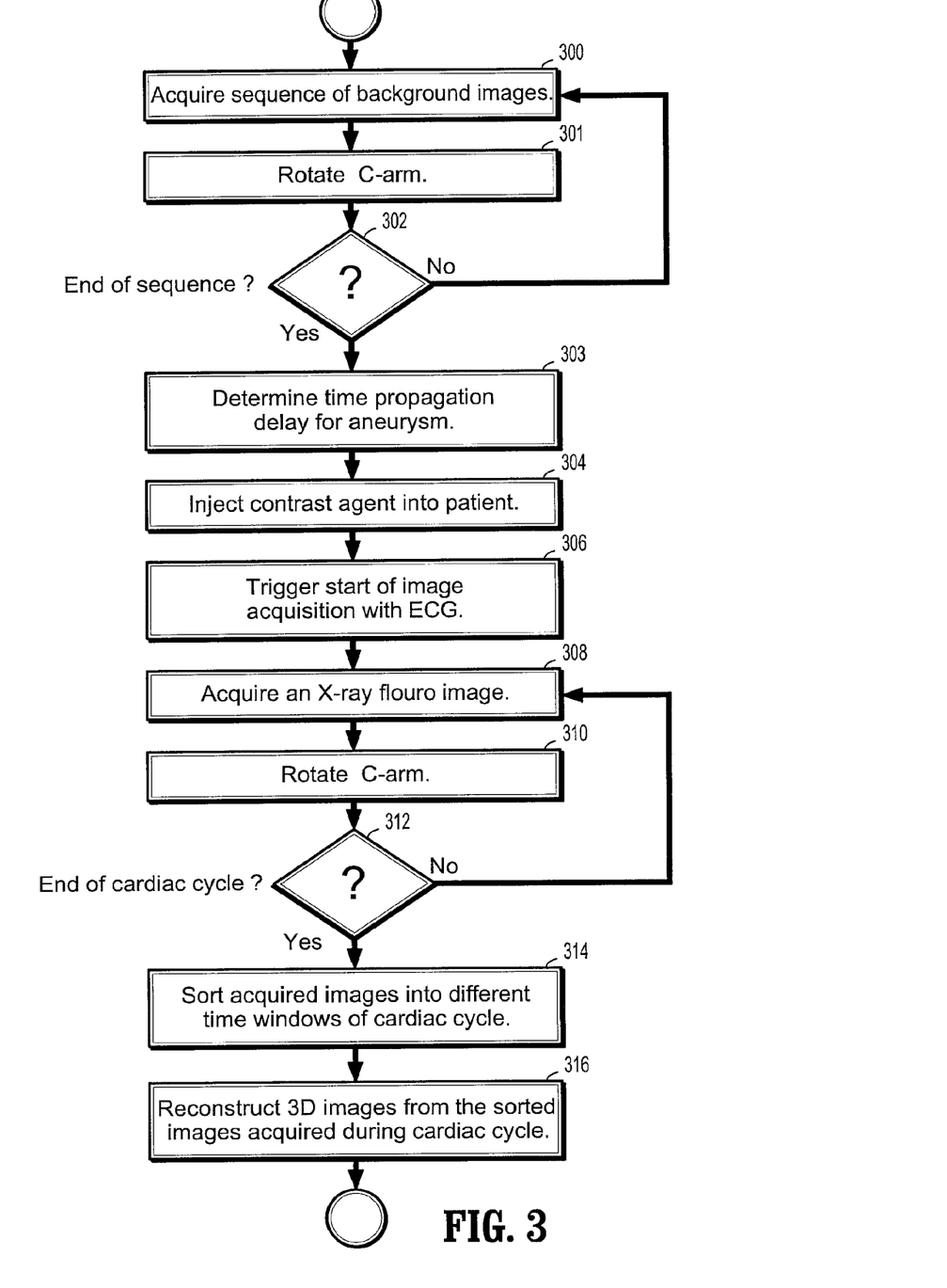
FIG. 3 is a flowchart of a method for performing 3D angiography imaging with ECG triggering according to an embodiment of the invention.

According to another embodiment of the invention, FIG. 3 is a flowchart of a method for performing 3D angiography imaging with electrocardiogram (ECG) triggering. Based on the ECG signal, projection images acquired in a rotational run are sorted into different time windows of the cardiac cycle, and are separately reconstructed. This can yield several 3D Angiography volumes, each at a different time in the cardiac cycle. Referring to the figure, a sequence of background images is acquired at step 300. These background images need to be acquired at the same positions and range as the images acquired with contrast subsequently. Therefore the background images are acquired with rotation in case of 3D imaging to be able to subtract image pairs and obtain. contrasted images like DSA images. Thus, the C-arm is rotated at step 301 until the end of the sequence at step 302. The pulsation of the aneurysm is delayed with respect to the beating of the heart as the blood pressure changes have to propagate from the heart to the aneurysm. According to an embodiment of the invention, this time delay is taken into account to optimally place the time windows, from which the projection images for 3D reconstruction are acquired, within the cardiac cycle. To measure the time delay, a fluoro sequence from a fixed viewpoint can be acquired, and the largest expansion and smallest contraction of the aneurysm within the cardiac cycle are determined at step 303, with the ECG signal as the reference clock. As before, at step 304, a contrast agent is injected, and the start of the acquisition cycle is triggered by the ECG at step 306, taking into account the propagation delay. An image is acquired at step 308, along with the ECG signal. To collect enough projection data, one may at step 310 either rotate the C-arm slower than in standard 3D Angiography acquisition, or rotate the C-arm back and forth at least once. At step 312, the ECG is checked to see if the end of the cardiac cycle has been reached. If not, the image acquisition system loops back to repeat steps 308 to 312. At step 314, the projection images acquired in the rotational run are sorted into different time windows of the cardiac cycle, and are separately reconstructed at step 316 yielding the 3D angiography volumes. As before, the background images are subtracted from the corresponding contrast enhanced images.

Figure 4:
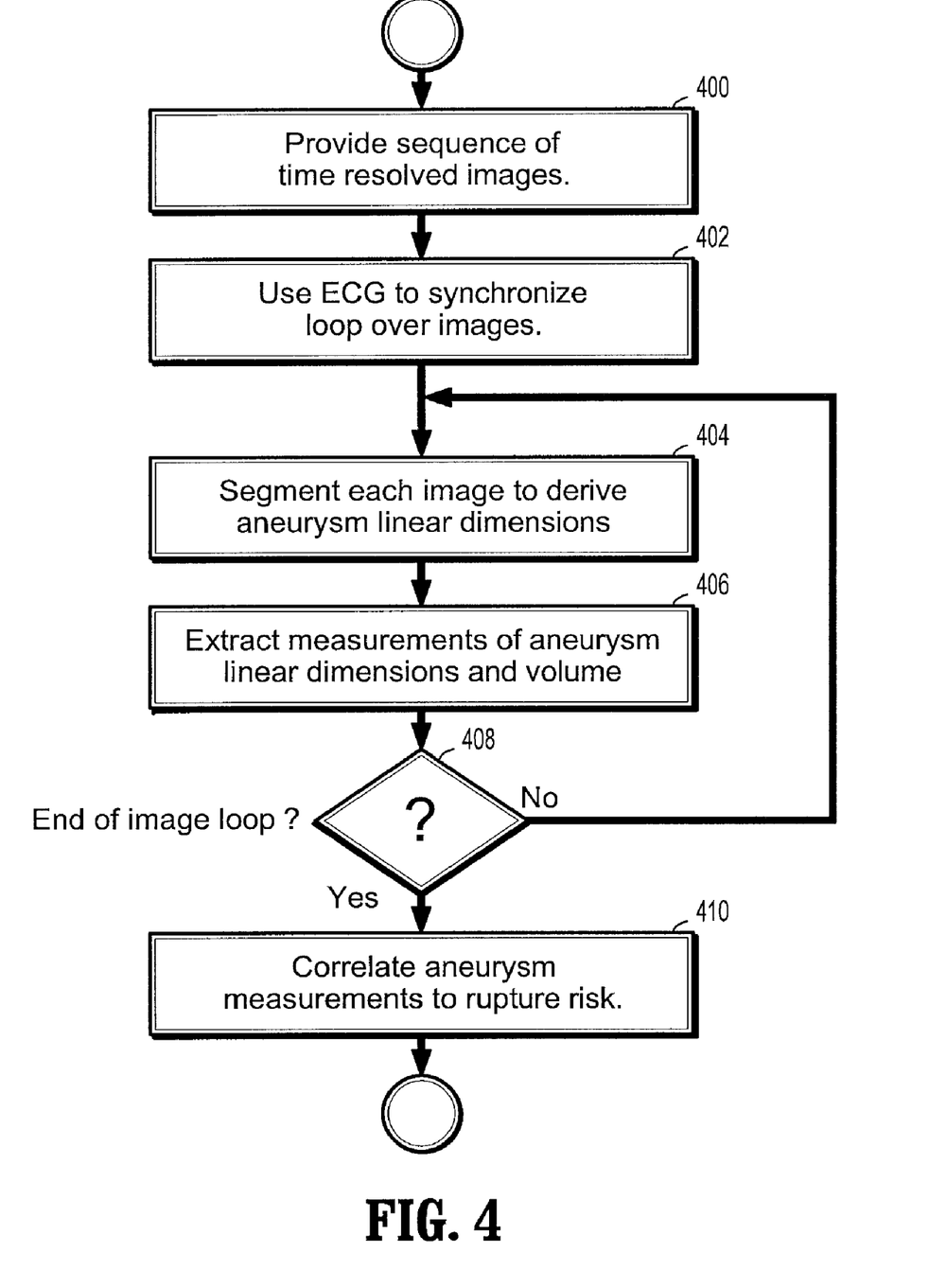
FIG. 4 is a flowchart of a method of deriving measurements for assessing rupture risk from the time-resolved images, according to an embodiment of the invention.

Future clinical studies may indicate how one could correlate the magnitude of linear dimension changes or volume changes during aneurysm pulsation with rupture risk. According to another embodiment of the invention, FIG. 4 is a flowchart of a method of deriving several measurements from the time-resolved images, and using those proven to correlate best with a diagnostic assessment of rupture risk. Referring to the figure, one or more sequences of time-resolved images, acquired by any of the methods as presented in FIGS. 1 to 3, are provided at step 400. A loop over these images begins at step 402, using the ECG signal to synchronize the different fluoro sequences. The linear dimensions of the aneurysm can be derived at step 404 from the 3D Angiography images acquired using the embodiment described by FIG. 3 by segmentation and integration. Sequences of image tuples, such as pairs, triplets, quadruplets, etc., depending on the number of image sequences available, can be used to extract volume measurements of the aneurysm. Alternatively, according to another embodiment of the invention, two or more high-frame rate fluoro sequences can be used to segment the aneurysm and its connected vessels, and to interpolate the 2D outlines into a 3D shape. Such interpolation methods are well known in the art. Measurements are extracted at step 406. Measurements include: (1) linear dimensions selected by geometrical shape of aneurysm (e.g. along direction of neck) and its variation over time; (2) Linear dimension selected by time-resolved measurement (e.g. direction of largest relative expansion) and its variation over time; and (3) Aneurysm volume and its variation over time. The variation over time can be a simple measure of maximal relative change. Alternatively, in a more complex approach, it can include the degree of non-linear motion exhibited by the aneurysm, which requires better time resolution in the imaging. After the image loop terminates at step 408, these dynamic aneurysm measurements are correlated with corresponding values derived from clinical studies at step 410. Once these correlations are clinically validated, the dynamic imaging of the aneurysm can be used with the methods described above for diagnostic assessment of rupture risk. Images can be acquired as described above and processed to extract the required measurements, and make the diagnosis based on the measurement results in reference to the previously validated risk assessment.

Figure 5:
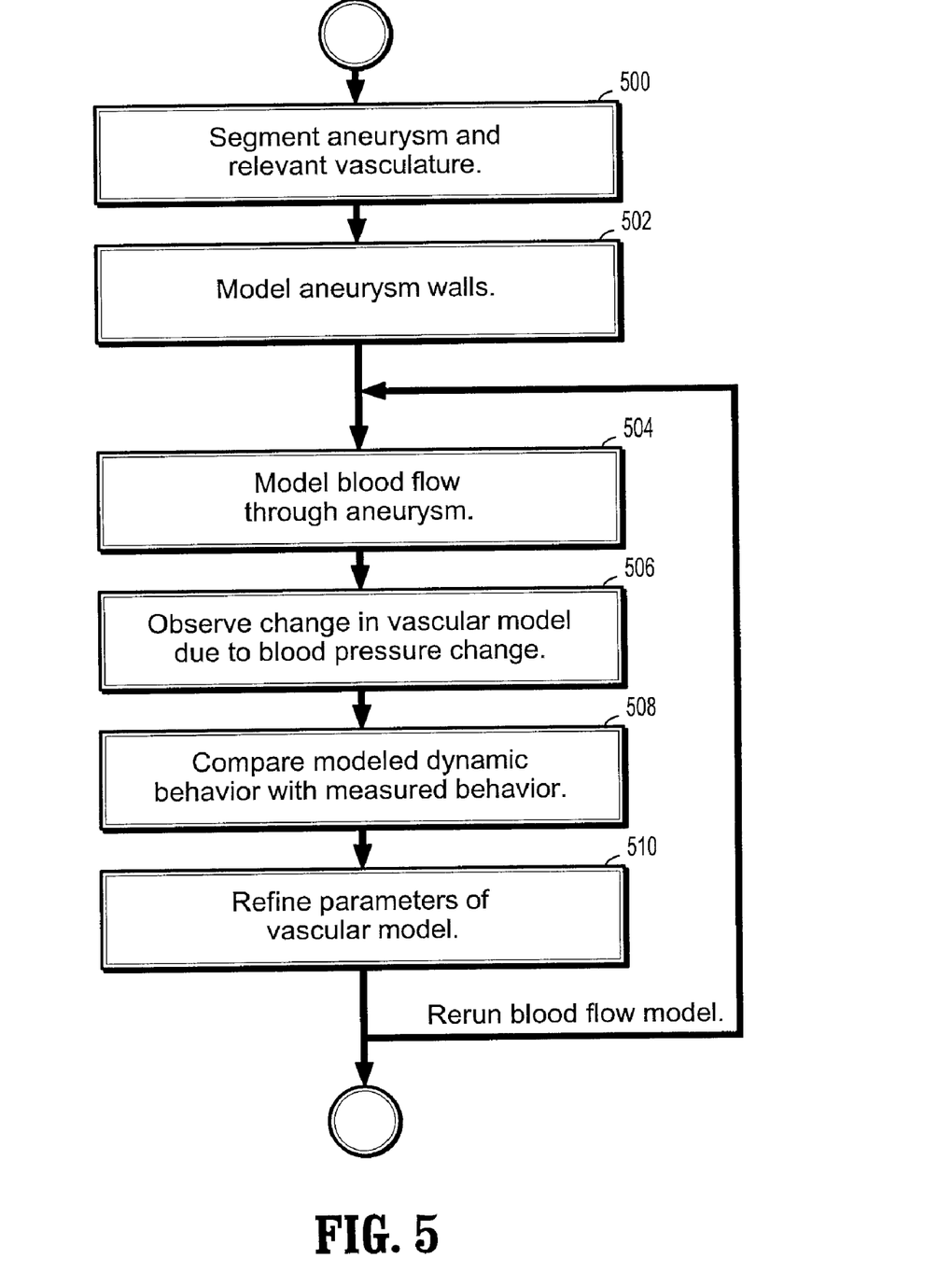
FIG. 5 is a flowchart of a method of modeling aneurysm behavior, according to an embodiment of the invention.

According to further embodiment of the invention, FIG. 5 is a flowchart of a method of modeling aneurysm behavior, for those aneurysm cases where a simple correlation of measurement and rupture risk is not conclusive. The dynamic behavior of the aneurysm can be measured as described above in connection with FIGS. 1 to 3, although the 3D DSA produced by the method of FIG. 3 is useful in this context. Referring to the figure, given this image data and extracted measurements, the relevant vasculature and the aneurysm are segmented at step 500, and the walls are modeled at step 502, e.g. with a finite element or boundary element model, and the blood flow through this system is modeled at step 504 by methods of computational fluid dynamics. As the blood pressure changes, a change in the vascular model can be observed at step 506. The model will start pulsating with a periodic pressure change. Using standard methods, by comparing the modeled dynamic behavior with the measured behavior at step 508, the elastic and other material parameters in the vascular model can be iteratively refined at step 510, and the blood flow modeling of step 506 to 508 can be repeated. In this way, time-resolved aneurysm imaging in combination with computational fluid dynamics and bio-mechanical modeling can lead to a realistic patient-specific modeling of aneurysms, and risk can be assessed in terms of stress and strain in the aneurysm wall, and the weakness of the wall can be determined in terms of the material parameters calculated in the model.

According to another embodiment of the invention, instead of DSA, CTA can be used with a cardiac imaging option, such as ECG gating/synchronization, to reconstruct several phases of the pulsating aneurysm during the cardiac cycle.

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 6:
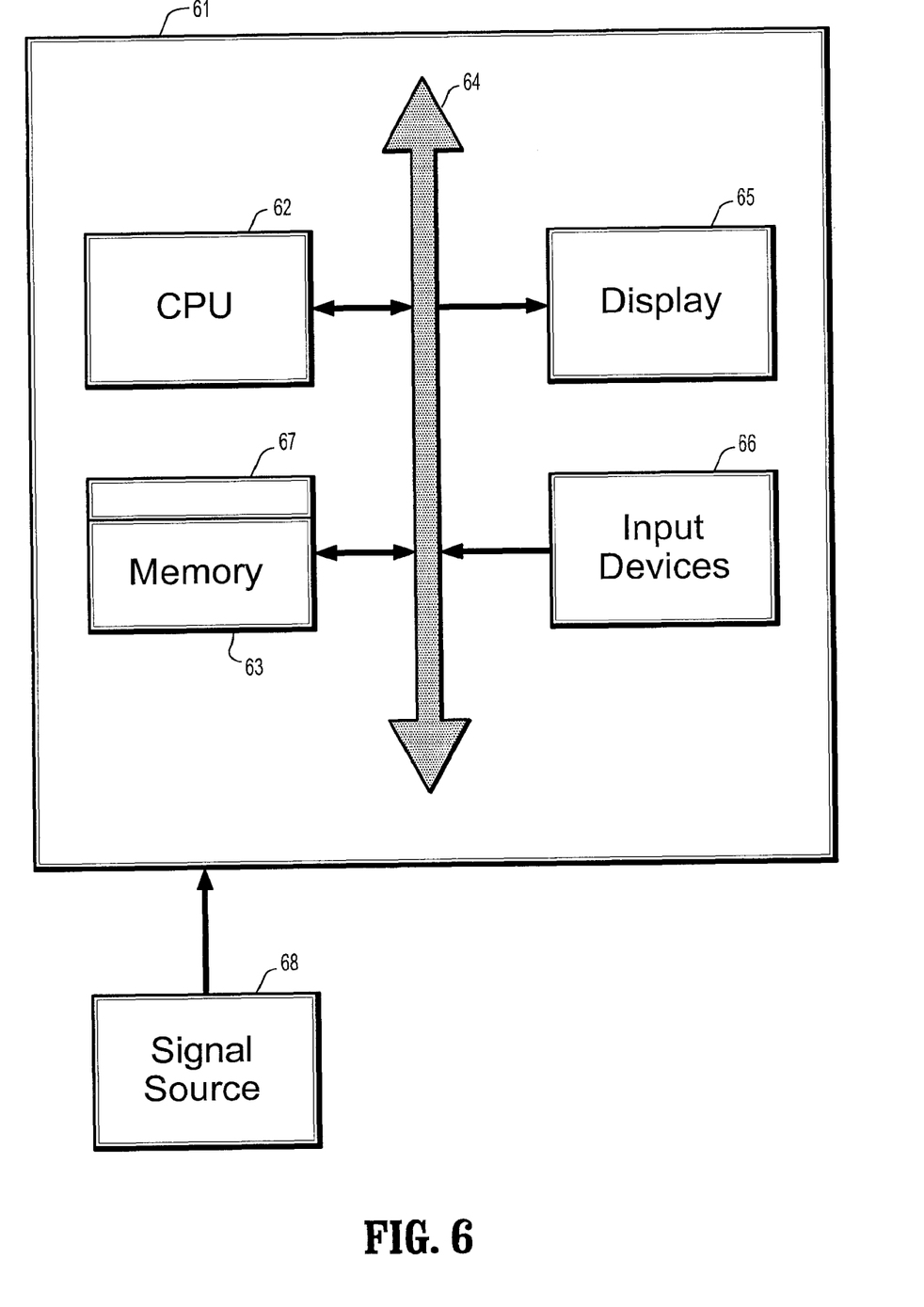
FIG. 6 is a block diagram of an exemplary computer system for implementing a method for time-resolved imaging of pulsating aneurysms, according to an embodiment of the invention.

FIG. 6 is a block diagram of an exemplary computer system for implementing a method for time-resolved flouro imaging of pulsating aneurysms, according to an embodiment of the invention. Referring now to FIG. 6, a computer system 61 for implementing the present invention can comprise, inter alia, a central processing unit (CPU) 62, a memory 63 and an input/output (I/O) interface 64. The computer system 61 is generally coupled through the I/O interface 64 to a display 65 and various input devices 66 such as a mouse and a keyboard. The support circuits can include circuits such as cache, power supplies, clock circuits, and a communication bus. The memory 63 can include random access memory (RAM), read only memory (ROM), disk drive, tape drive, etc., or a combinations thereof. The present invention can be implemented as a routine 67 that is stored in memory 63 and executed by the CPU 62 to process the signal from the signal source 68. As such, the computer system 61 is a general purpose computer system that becomes a specific purpose computer system when executing the routine 67 of the present invention.

The computer system 61 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method of assessing rupture risk of an aneurysm from time-resolved images comprising the steps of:
   injecting a contrast enhancing agent into a patient with an aneurysm;
   acquiring a sequence of 2D X-ray images of said aneurysm over a cardiac cycle using an electrocardiogram (ECG) signal to trigger said acquisition of said image sequence;
   shifting a trigger point in the cardiac cycle image acquisition by a time shorter than an exposure time for a 2D X-ray image, and acquiring another sequence of images using said shifted trigger point
   extracting linear or area measurements of said aneurysm from said sequence of images; and
   correlating the extracted aneurysm measurement values to clinically known values to assess a rupture risk of said aneurysm.

2. The method of claim 1, further comprising acquiring a plurality of image sequences from multiple viewpoints using the ECG trigger to establish correspondences between images from different sequences of said plurality of sequences in relation to a cardiac phase.

3. The method of claim 2, further comprising using a sequence of corresponding image tuples from said different sequences to extract volume measurements of said aneurysm, and correlating these values to clinically known values to assess a rupture risk of said aneurysm.

4. The method of claim 1, further comprising acquiring a sequence of background 2D X-ray images acquired without using said injected contrast enhancing agent, and subtracting said background images from said contrast enhanced images that correspond in relation to the cardiac phase.

5. The method of claim 2, further comprising segmenting said aneurysm in each image of each of said image sequences and interpolating 2D segmented outlines into a 3D shape of said aneurysm.

6. The method of claim 1, further comprising providing a bi-plane attaching X-ray imaging apparatus, adjusting a viewing direction of said C-arm for image acquisition, and acquiring pairs of images from different viewing directions and displaying said pair of images on different display monitors.

7. The method of claim 1, further comprising adjusting a C-arm orientation after acquiring a sequence of images, wherein said C-arm attaches the X-ray imaging apparatus, and performing another sequence of image acquisitions.

8. The method of claim 1, further comprising determining a variation over time of said linear or area measurements of said aneurysm by calculating a maximal relative change of each linear or area measurement.

9. The method of claim 3, further comprising determining a variation over time of said volume measurements of said aneurysm by calculating a maximal relative change of said volume measurement.

10. The method of claim 8, further comprising determining a degree of non-linear motion of said aneurysm as its linear or area measurements vary over time using said ECG signal to time resolve said acquired images.

11. A program storage device readable by a computer, tangibly embodying a program of instructions executable by the computer to perform the method steps for assessing rupture risk of an aneurysm from time-resolved images, said method comprising the steps of:
    injecting a contrast enhancing agent into a patient with an aneurysm;
    acquiring a sequence of 2D X-ray images of said aneurysm over a cardiac cycle;
    extracting linear or area measurements of said aneurysm from said sequence of images;
    determining a variation over time of said linear or area measurements of said aneurysm by calculating a maximal relative change of each linear or area measurement;
    determining a degree of non-linear motion of said aneurysm as its linear or area measurements vary over time using said ECG signal to time resolve said acquired images; and
    correlating the extracted aneurysm measurement values to clinically known values to assess a rupture risk of said aneurysm.

12. The computer readable program storage device of claim 11, the method further comprising using an electrocardiogram (ECG) signal to trigger said acquisition of said image sequence.

13. The computer readable program storage device of claim 12, the method further comprising acquiring a plurality of image sequences from multiple viewpoints using the ECG trigger to establish correspondences between images from different sequences of said plurality of sequences in relation to a cardiac phase.

14. The computer readable program storage device of claim 13, the method further comprising using a sequence of corresponding image tuples from said different sequences to extract volume measurements of said aneurysm, and correlating these values to clinically known values to assess a rupture risk of said aneurysm.

15. The computer readable program storage device of claim 12, the method further comprising acquiring a sequence of background 2D X-ray images acquired without using said injected contrast enhancing agent, and subtracting said background images from said contrast enhanced images that correspond in relation to the cardiac phase.

16. The computer readable program storage device of claim 12, the method further comprising shifting a trigger point in the cardiac cycle for starting said image acquisition by a time shorter than an exposure time for a 2D X-ray image, and acquiring another sequence of images using said shifted trigger point.

17. The computer readable program storage device of claim 13, the method further comprising segmenting said aneurysm in each image of each of said image sequences and interpolating 2D segmented outlines into a 3D shape of said aneurysm.

18. The computer readable program storage device of claim 11, the method further comprising providing a bi-plane C-arm attaching X-ray imaging apparatus, adjusting a viewing direction of said C-arm for image acquisition, and acquiring pairs of images from different viewing directions and displaying said pair of images on different display monitors.

19. The computer readable program storage device of claim 11, the method further comprising adjusting a C-arm orientation after acquiring a sequence of images, wherein said C-arm attaches the X-ray imaging apparatus, and performing another sequence of image acquisitions.

20. The computer readable program storage device of claim 14, the method further comprising determining a variation over time of said volume measurements of said aneurysm by calculating a maximal relative change of said volume measurement.

* * * * *